US009593143B2

(12) United States Patent
Colaco et al.

(10) Patent No.: US 9,593,143 B2

(45) **Date of Patent: *Mar. 14, 2017**

(54) METHOD FOR PURIFYING PROTEIN COMPLEXES

(75) Inventors: Camilo Colaco, Cambridge (GB); Kamram Salim, Cambridge (GB)

(73) Assignee: IMMUNOBIOLOGY LTD, Cambridge (GB)

(*) Notice: Subject to any disclaimer, the term of this patent is extended or adjusted under 35 U.S.C. 154(b) by 249 days.

This patent is subject to a terminal disclaimer.

(21) Appl. No.: 13/062,465

(22) PCT Filed: Sep. 7, 2009

(86) PCT No.: PCT/GB2009/051133

§ 371 (c)(1), (2), (4) Date: May 11, 2011

(87) PCT Pub. No.: WO2010/026432

PCT Pub. Date: Mar. 11, 2010

(65) Prior Publication Data

US 2011/0206725 A1 Aug. 25, 2011

(30) Foreign Application Priority Data

Sep. 5, 2008 (GB) .................................. 0816242.2

(51) Int. Cl.

| | |
|---|---|
| ***C07K 1/32*** | (2006.01) |
| ***A61K 39/00*** | (2006.01) |
| ***C07K 1/18*** | (2006.01) |
| ***A61K 39/04*** | (2006.01) |
| ***A61K 39/095*** | (2006.01) |
| ***C07K 14/00*** | (2006.01) |

(52) U.S. Cl.

CPC ............ *C07K 1/18* (2013.01); *A61K 39/0011* (2013.01); *A61K 39/04* (2013.01); *A61K 39/095* (2013.01); *C07K 14/00* (2013.01); *A61K 2039/5256* (2013.01); *C07K 2319/30* (2013.01); *C12N 2710/14143* (2013.01); *C12N 2760/16122* (2013.01); *C12N 2770/24222* (2013.01)

(58) Field of Classification Search

CPC ................ A61K 39/0011; A61K 39/04; A61K 2039/5154; A61K 2039/5156; A61K 2039/5158; A61K 38/17; A61K 39/39; A61K 2039/57; A61K 39/12; A61K 47/4833; A61K 39/095; A61K 39/0002; A61K 39/08; A61K 39/01; A61K 2039/6043; A61K 2300/00; A61K 38/1709; A61K 2039/622; A61K 39/00; A61K 2039/5152; A61K 51/088; C12Q 2565/137; C12Q 1/6886; G01N 1/34; G01N 30/02; G01N 33/6851; C07K 1/18; C07K 14/00; C07C 17/38; C12Y 304/22063; C12N 2710/16634; C12N 2710/20022; C12N 2710/16134

See application file for complete search history.

(56) References Cited

U.S. PATENT DOCUMENTS

| | | | | |
|---|---|---|---|---|
| 5,961,979 | A * | 10/1999 | Srivastava | 424/193.1 |
| 5,997,873 | A * | 12/1999 | Srivastava | 424/193.1 |
| 6,017,540 | A * | 1/2000 | Srivastava et al. | 424/193.1 |
| 6,030,618 | A * | 2/2000 | Srivastava | 424/184.1 |
| 6,048,530 | A * | 4/2000 | Srivastava | 424/193.1 |
| 6,455,503 | B1 * | 9/2002 | Srivastava | 424/450 |
| 6,875,849 | B2 * | 4/2005 | Graner et al. | 530/412 |
| 6,984,384 | B1 * | 1/2006 | Subjeck et al. | 424/184.1 |
| 7,378,096 | B2 * | 5/2008 | Subjeck et al. | 424/184.1 |
| 7,494,785 | B1 * | 2/2009 | Shannon et al. | 435/69.1 |
| 2003/0031661 | A1 * | 2/2003 | Graner et al. | 424/94.63 |

FOREIGN PATENT DOCUMENTS

| | | | |
|---|---|---|---|
| EP | 1531160 A1 | | 5/2005 |
| WO | WO 01/14411 | * | 3/2001 |
| WO | WO03/092624 | * | 11/2003 |

OTHER PUBLICATIONS

Peng et al. J. immunological methods 1997, vol. 20, issue 1, pp. 13-21.*

Przepiorka D et al. Mol Med Today. Nov. 1998;4(11):478-84.*

HSP70 (human) PhosphoSitePlus published from Cell Signaling Technology Inc., 2003-2013, pp. 1-3.*

HSP90 (human) PhosphoSitePlus published from Cell Signaling Technology Inc. 2003-2013, pp. 103.*

Floto et al. Science 2006, vol. 314, No. 5798, pp. 454-458.*

Heike et al. (Biochemical Pharmacology 1999, vol. 58, pp. 1381-1387).*

Cell Signaling Technology Inc, published on 2003 at PhosphoSitePlus, pp. 1-3, 1-4 and1-5.*

Palleros et al, "hsp70-Protein Complexes Complex Stability and Conformation of Bound Substrate Protein", 269(18):13107-14 (1994).

Ion Exchange Chromatography—Principles and Methods, Amersham Pharmacia Biotech (1999).

Menoret et al., Purification of multiple heat shock proteins from a single tumor sample, *J. Immunol. Methods*, 237:119-30 (2000).

* cited by examiner

*Primary Examiner* — Bao Li

(74) *Attorney, Agent, or Firm* — Marshall, Gerstein & Borun LLP

(57) ABSTRACT

The present invention provides a method for the purification of complexes comprising a stress protein complexed to a peptide or peptide fragment, from a source mixture, typically a cell lysate. The improved method of the invention provides for protein complexes to be purified using ion exchange based methods, without the need to use chemicals such as chaotropes and ampholytes. The purified complexes can be used as the immunogenic determinant in vaccine compositions for the treatment or prevention of infectious diseases or cancerous conditions.

13 Claims, 8 Drawing Sheets

RUN 2 09/01/15 TUMOUR LYSATE 0.57mg/mL

Load 9mL (@5mg)
Flow 1mL/min
STEP elution 0, 250mM, 500mM, 1M
Ft pool 1 and 2
250mM Pool 9, 10, 11.

500mM Pool 19 and 20
Buffer 1
40mM Tris pH6.8, 0.1% Triton, 1mM Mg, 1mM ADP
Buffer 2
40mM Tris pH6.8, 0.1% Triton, 1mM Mg,1mM ADP 1M NaCl 10µl load on 4-12% Gel MES Running buffer
Pooled samples. Peak 1 and Peak 2 were Buffer exchanged into BUFF 1 plus 150mM NaCl.

METHOD FOR PURIFYING PROTEIN COMPLEXES

This application is a U.S. National Phase of International Patent Application No. PCT/GB2009/051133, filed Sep. 7, 2009, which claims priority to Great Britain Patent Application No.: 0816242.2, filed Sep. 5, 2008, the entire disclosures of which are incorporated herein by reference.

FIELD OF THE INVENTION

The present invention relates to novel methodology for the purification of protein complexes. In particular, there is provided a method for the production of protein complexes comprising heat shock proteins coupled to peptide fragments. The invention further extends to the use of protein complexes provided according to the present invention in the preparation of vaccine compositions for the prevention and treatment of infectious diseases and cancer.

BACKGROUND OF THE INVENTION

Vaccination is widely accepted as the favoured approach to tackle the global healthcare burden of infectious disease and cancer. However, despite significant advances in relation to our understanding of the molecular biology relating to infectious disease and cancers, the development of effective vaccines in these areas has been limited. The most effective vaccines developed have used live, attenuated organisms, however, the safety risk associated with such attenuated pathogens reverting to virulence, has restricted their widespread use. A further major barrier preventing the wide scale development and use of more effective vaccines is the limitation associated with the ability to identify candidate pathogen derived proteins that will elicit broad protective immunity in a specific manner against variant strains of microbial pathogens, when administered as part of a vaccine composition.

One particular approach that shows the promise of conferring broad, protective immunity is the use of stress protein complexes as vaccines against infectious disease and cancer (Colaco et al., (2004) Biochem Soc Trans 32:626-628 and Zeng et al., (2006) Cancer Immunol Immunother 55:329-338)). It has also been widely documented that heat shock protein/antigenic peptide complexes are efficacious as vaccines against specific cancers (U.S. Pat. No. 5,997,873; U.S. Pat. No. 5,935,576, U.S. Pat. No. 5,750,119, U.S. Pat. No. 5,961,979 and U.S. Pat. No. 5,837,251). Colaco and colleagues have shown that pathogen derived stress protein-peptide complexes isolated from heat-shocked BCG cells induced T-helper 1 (Th1) mediated immune responses in a vaccinated subject, which conferred protective immunity against a live challenge in a murine aerosol challenge model of pulmonary tuberculosis (International Patent Application No. WO 01/13944). Moreover, it has been shown in International Patent Application Nos. WO 02/20045, WO 00/10597 and WO 01/13943 that stress protein complexes isolated from pathogens or pathogen infected cells are effective as the immunogenic determinant within vaccines against infectious diseases.

Heat shock proteins (hsps) form a family of highly conserved proteins that are widely distributed throughout the plant and animal kingdoms. On the basis of their molecular weight (kDa), the major heat shock proteins are grouped into six different families: small (hsps of 20-30 kDa); hsp40; hsp60; hsp70; hsp90; and hsp100. Although heat shock proteins were originally identified in cells subjected to heat stress, they have been found to be associated with many other forms of stress, such as infections, osmotic stress, cytokine stress and the like. Accordingly, heat shock proteins are also commonly referred to as stress proteins (SPs) on the basis that their expression is not solely caused by a heat stress. Members of the hsp60 family include the major chaperone GroEL. These form multimeric complexes with co-chaperones such as GroES. Many microbial pathogens have additional hsp60 families that form distinct complexes from GroEL and some hsp60 family members may be more immunogenic, such as the hsp65 of mycobacteria. Members of the hsp70 family include DnaK and these hsp 70 family members also form multimeric complexes with co-chaperones such as DnaJ. Other major heat shock proteins include the AAA ATPases, the Clp proteins, Trigger factor, Hip, HtpG, NAC, Clp, GrpE, SecB and prefoldin.

Stress proteins are ubiquitously expressed in both prokaryotic and eukaryotic cells, where they function as chaperones in the folding and unfolding of polypeptides. A further role of stress proteins is to chaperone peptides from one cellular compartment to another and, in the case of diseased cells, stress proteins are also known to chaperone viral or tumour-associated peptides to the cell-surface. The chaperone function of stress proteins is accomplished through the formation of complexes between stress proteins and the chaperoned polypeptide. Such polypeptides may include peptide fragments.

In the immune response, heterologous polypeptides, or polypeptide fragments complexed with the stress proteins form stress protein-peptide complexes, which may be referred to as heat shock protein complexes (HspCs). HspCs are captured by antigen presenting cells (APCs) to provide a source of antigenic peptides which can be loaded onto major histocompatibility complex (MHC) molecules for cell surface presentation to the T-cells of the immune system.

HspCs have been widely studied as cancer vaccines and methods have been developed for the isolation of HspCs from tumour cells for use as effective vaccines (U.S. Pat. No. 5,997,873; U.S. Pat. No. 5,935,576; U.S. Pat. No. 5,750,119, U.S. Pat. No. 5,961,979 and U.S. Pat. No. 5,837,251). However, these methods resulted in the isolation of restricted families of heat shock proteins, and therefore specifically excluded the use of multiple chaperone proteins as the immunogenic determinant in vaccines. The use of HspCs as cancer vaccines can be significantly improved by the use of multiple chaperone proteins, in particular heat shock proteins (reviewed in Zeng et. al. Cancer Immunol. Immunother (2006) 55: 329-338) and thus methods have been developed for the purification of multiple chaperone proteins and chaperone protein complexes for use in vaccines. For example, U.S. Pat. No. 6,875,849 discloses the use of free-solution isoelectric focusing (FF-IEF) for the purification of HspCs from tumours for use as cancer vaccines.

The present inventors have previously found that FF-IEF can also be used to isolate HspCs from pathogens and infected cells for use as the immunogenic determinant in vaccine compositions for the prevention and treatment of infectious diseases. However, a key limitation of this technique has been the difficulties associated with developing a large scale FF-IEF instrument to produce the quantities of heat shock protein/peptide complexes (HspCs) which would be required for large scale, commercial GMP vaccine manufacture. Additionally, FF-IEF separates complexes on the basis of their isoelectric points (pI) and the process of free-flow focussing is slow with a typical run time of 4 hours, during which high levels of protein degradation result, severely limiting the use of FF-IEF in large scale production of purified heat shock protein-peptide complexes. Furthermore, the use of chaotropes, such as urea, to maintain protein solubility during purification can result in the disruption of some heat shock protein-peptide complexes. Moreover, the use of ampholytes (ampholines) to produce the pH gradient required during the FF-IEF process results in the introduction of a further contaminant, in addition to the chaotropes, in the heat shock protein-peptide containing preparations. Such contaminants, being immunogenic themselves and also unacceptable to Regulatory Authorities, pose a significant barrier to the use of FF-IEF in the manufacture of heat shock protein-peptide complex containing vaccine compositions.

SUMMARY OF THE INVENTION

According to a first aspect of the present invention there is provided a method for the purification from a source mixture of a target stress protein complex, wherein said complex is formed between a stress protein and a polypeptide or polypeptide fragment, from a source mixture, the method comprising the steps of:

(i) providing a source mixture comprising at least one target stress protein complex formed from a stress protein complexed to a polypeptide fragment, (ii) determining the isoelectric point (pI) of the at least one target stress protein complex which is to be purified from the source mixture;

(iii) subjecting the source mixture to purification using ion exchange, wherein the cell lysate is buffered using a buffer to a pH within 2 units of the pI of the target stress protein complex, and wherein a salt gradient is used to elute the target stress protein complex.

Typically the method provides for the purification of a plurality of heat shock protein-peptide complexes (HspCs) from the source mixture. In certain embodiments, the heat shock protein-polypeptide complexes comprise heat shock proteins of the same family, for example heat shock proteins from the HSP70 family. In further embodiments, the complexes comprise heat shock proteins from different heat shock protein families. In certain embodiments, the complexes comprise a polypeptide which is a tumour specific antigen. In certain further embodiments, the polypeptide is derived from a pathogenic organism which causes an infectious disease in a host.

In certain embodiments the method further comprises the step of preparing a clarified cell lysate from the source mixture comprising the identified target stress protein complex. In certain embodiments, the cell lysate, which may also be referred to as a cellular lysate, is derived from a eukaryotic cell. In certain further embodiments, the cell lysate is derived from a bacterial cell. In certain further embodiments, the cell lysate is derived from a cancerous cell or from cells isolated from a tumour mass.

In certain embodiments, the buffer does not include chaotropes and/or surfactants and/or ampholytes. Chaotropes (also known as chaotropic agents, or chaotropic reagents) include urea, guanidine hydrochloride and lithium percolate. Chaotropes are known to act as protein denaturants, causing a protein to unfold and a resultant change in three dimensional structure. Ampholytes are molecules which contain both acidic and basic groups. They exist mostly as zwitterions (a chemical compound which has a net charge of zero) in a certain range of pH. Surfactants may include anionic surfactants, such as SDS, cationic surfactants, such as CTAC, HTAB and DTAB, non-ionic surfactants, such as Tween 20, and zwitterionic surfactants, such as DAPS. In certain embodiments, the buffer does not contain a chaotrope, an ampholyte or a surfactant.

Typically the buffer does not include urea and/or ampholytes, or the like.

Following extensive experimentation, the present inventors have identified an improved method for the purification of stress protein-polypeptide complexes, such as HspCs that can be used for vaccine manufacture. This method separates the protein complexes on the basis of surface charge rather than isoelectric point. In particular, a purification method has been identified which allows for the rapid purification of at a protein complex comprising a stress protein complexed to a peptide fragment, wherein the yield of purified product is sufficient to allow the preparation of a commercially acceptable amount of the protein complexes for use in the preparation of a vaccine composition. Advantageously, the purified protein complexes can be used in the preparation of a vaccine preparation without the use of pharmaceutically unacceptable additives in the purification process. The purification method further advantageously reduces or ameliorates degradation and loss of function of the purified protein complexes, whilst concomitantly removing the need to use chaotropes or other chemicals such as surfactants to increase solubility of the protein complex undergoing purification. Most surprisingly, the heat shock protein/antigenic peptide complex (HspC) enriched preparations (HEPs) purified using the improved methodology of the present invention resulted in significantly enhanced immunity being raised in a vaccinated subject, when compared to the immunity mediated against similar complexes isolated using standard FF-IEF methodology.

Source Mixture

In certain embodiments, the source mixture is a mixture which comprises at least one stress protein/peptide fragment complex (for which purification is desired) and one or more contaminants. Non-limiting examples of contaminants present in the source mixture may include: host cell proteins other than stress proteins, host cell metabolites, host cell constitutive proteins, immunodominant proteins, nucleic acids, endotoxins, chemical product related contaminants, lipids, media additives and media derivatives.

In certain embodiments, the source mixture is, or is derived from a cell lysate, or a cell homogenate. In certain embodiments, the cell lysate or homogenate is derived from a prokaryotic cell, typically a pathogenic prokaryotic cell, wherein said prokaryotic cell may be an intracellular pathogenic bacteria or an extracellular pathogenic bacteria. In certain further embodiments, the cell lysate may be derived from a cell infected with a prokaryotic cell. In further embodiments, the cell lysate or homogenate is derived from a eukaryotic cell, such as a eukaryotic cell infection with a pathogen such as a prokaryotic pathogen. In certain embodiments, the cell lysate or homogenate is derived from a tumour cell, a cancerous cell mass or tissue, or a cell derived from a biopsy. In certain embodiments, the cells are cells derived from cell culture which are transformed or transfected. In certain further embodiments, the cell lysate or homogenate can be obtained directly from a host cell or organism producing the polypeptide, or from a cell infected by a pathogenic organism. Further examples of source mixtures that can be purified using the method of the present invention include harvested cell culture fluid, cell culture supernatant and conditioned cell culture supernatant.

In embodiments where the source mixture is derived from, or comprised of a cell lysate, the lysate may be obtained by any suitable means known to the person skilled in the art, including, but not limited to: mechanical means, such as sonication, cavitation, freeze-thaw cycles, the use of a cell homogeniser such as a French press, Dounce homogeniser or motor driven glass/TEFLON homogenizer; cell lysis using a detergent; or osmotic lysis by bringing the cells into contact with a hypotonic buffer or hypertonic buffer as required.

In certain embodiments where cell lysis is used to produce the source mixture, proteinase inhibitors may further be added to the source mixture.

In certain embodiments, where the source mixture is derived from a homogenised cell preparation, such as a cell lysate or a tissue sample, the homogenate may be clarified using centrifugation. In such embodiments, the cell lysated can be centrifuged, at least once, for example at 10000 g for 30 minutes. The supernatant can then be collected and subjected to further centrifugation, or prepared for purification using an ion exchange based methodology described herein. In certain further embodiments the centrifugation step may be replaced or complimented by a filtration step.

In certain embodiments, the source mixture is a proteinaceous mixture for example a solution comprised of a plurality of proteins. In certain further embodiments, the source mixture can be a cell lysate derived from cancerous cells, pathogenic organisms, cells infected with pathogenic organisms, or cell cultures comprising pathogenic organisms, or cells infected therewith.

In certain embodiments, the method of the invention can be use to extract, purify and/or obtain a protein complex from a natural or biosynthetic source. In certain further embodiments, the method can be used to purify a synthetic or recombinant stress protein complex from a cell culture or other protein mixture.

After ion exchange, in certain embodiments, the purified target stress protein complex is present within at least one fraction, such as an eluate fraction. Typically the at least one fraction comprises one or more stress protein/peptide complex. Said fraction may be referred to as a purified product or purification product, and may further be called a heat shock protein/antigenic peptide complex (HspC) enriched preparation (HEP).

Without wishing to be bound by theory, the inventors have identified that an enhanced immune response can be mounted in a subject who is administered a vaccine composition which comprises, as the immunogenic determinant, stress protein/antigenic peptide fragment complexes which are derived from a cancerous cell, a pathogenic cell, a cell infected by a pathogenic organism, or a cell which has been genetically modified such that it expresses a heterologous protein which is derived from a cancerous cell or a pathogen which causes an infectious disease in a host, wherein the heterologous protein causes an immune response to be mounted there-against when administered to a subject. As such, in certain embodiments, the purified stress protein complexes may typically comprise a mixture of antigenic peptide/heat shock protein complexes.

Heat Shock Protein

In certain embodiments, the heat shock protein complex may also be known as a stress protein complex.

In certain embodiments, the heat shock protein can be any suitable heat shock or stress protein which is present in the cell lysate which is to be purified, and which can therefore be isolated therefrom. In certain embodiments, the heat shock protein may be derived from any one of the heat shock protein families comprising, but not limited to: hsp20-30 kD; hsp40; hsp60; hsp70; hsp90; and hsp100. In certain further embodiments, the heat shock may be a protein which is classed as a chaperone protein. Such a protein may include, but is not limited to, proteins selected from the group consisting of: calrecticulin, hsp40, hsp70, hsp72, hsp90, grp94, grp75 BiP/grp78, grp75/mt and gp96.

In certain embodiments, the target stress protein complex comprises a heat shock protein/antigenic peptide fragment complex derived from a host cell which has been genetically modified to constitutively express stress protein genes, and/or express a heterologous protein, such as an antigenic peptide or peptide fragment. In certain further embodiments, the cell may be a host cell expressing a heterologous gene, for example an insect cell infected with a baculovirus vector construct comprising an antigenic gene of interest. In yet further embodiments, the cell may be a cancerous cell derived from a human or animal subject.

In certain embodiments, where a mixture of complexes is provided, this mixture can comprise heat shock proteins of one particular family, for example, hsp70 or hsp60. In such an embodiment, therefore, the method of the present invention would provide a method for the purification of all complexes comprising a hsp70 or a hsp60 heat shock protein complexed to an (antigenic) peptide fragment, irrespective of the identity, molecular weight or size of the antigenic peptide or peptide fragment.

In certain further embodiments, the heat shock protein/antigenic peptide complex (HspC) enriched preparations (HEP) comprises heat shock proteins derived from different stress protein families, such as hsp65 and hsp70, said families being co-purified using the method of this aspect of the invention. In certain embodiments, the stress protein complexes have a molecular weight in the range of 50 KDa to 900 KDa. In certain further embodiments, the heat shock protein/antigenic peptide complex (HspC) enriched preparations (HEPs) may consist of, or consist essentially of heat shock proteins from the same family as defined by molecular weight, for example the HSP70 family.

Antigenic Polypeptide Fragment

In certain embodiments, the polypeptide is a peptide fragment, that is, the peptide fragment is a fragment of a larger protein, peptide or polypeptide. Typically the peptide is an antigenic peptide. A peptide is an antigenic peptide if a T cell mediated immune response can be raised against it, following administration of a complex comprising the peptide to a subject.

Typically, the polypeptide is derived from a pathogen, or a cell infected with a pathogen, wherein an immune response is desired against the pathogen in order to confer protective immunity. In certain further embodiments, the polypeptide is derived from a non-pathogenic variant of a pathogen, wherein an immune response which is mediated against said polypeptide confers protective immunity against the pathogen from which the non-pathogenic variant is derived, or to which the non-pathogenic variant is related. In certain further embodiments, the polypeptide is derived from a malignant or cancerous cell, or a cell lysate containing the same, wherein the polypeptide or peptide fragment is a tumour associated antigen.

In certain embodiments, the peptide is complexed to the stress protein in a non-covalent manner. In certain further embodiments, the peptide is complexed to the stress protein by means of a covalent bond.

In certain embodiments, the peptide fragment is an antigenic peptide fragment derived from a pathogenic organism wherein the pathogenic organism typically causes an infectious disease in a host. In certain embodiments, the pathogenic cell may be a prokaryotic cell, such as a gram positive or gram negative bacteria, or an intracellular or extracellular bacterial pathogen. In certain further embodiments, the pathogen is a viral pathogen, or a peptide fragment derived therefrom. In certain further embodiments, the pathogen may be a protozoa, a parasite or a fungi, such as a yeast.

In certain embodiments, the pathogen from which the antigenic peptide is derived may be selected from the group consisting of, but not limited to: members of the genus *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma.*

In certain embodiments, the antigenic peptide fragment may be a viral peptide. The virus from which the peptide is derived may be selected from the group consisting of, but not limited to: human immunodeficiency virus (HIV), hepatitis A virus (HAV), hepatitis B (HBV), hepatitis C(HCV), any other hepatitis-associated virus, human papillomavirus (HPV) and especially high-risk oncogenic human papillomavirus types, Kaposi's Sarcoma-Associated Herpesvirus (KSHV) (also known as Human Herpesvirus-8 (HHV-8)), Herpes Simplex virus (HSV) (any subtype), Respiratory Syncytial Virus (RSV) and associated respiratory viruses, Influenza viruses, such as influenza A, coronaviruses including SARS-associated Coronavirus (SARS-CoV), rhinovirus, adenovirus, SIV, rotavirus, human papilloma virus, arbovirus, measles virus, polio virus, rubella virus, mumps virus, papova virus, cytomegalovirus, varicella-zoster virus, varicella virus, huntavirus and any emergent virus, in particular Ebola virus, Marburg virus, West Nile virus (WNV), St Louis Encephalitis virus (SLEV), Rift Valley Fever virus (RVFV) and other members of the Bunyaviridae. Influenza A viruses can be divided into subtypes according to their surface proteins, hemagglutinin (HA or H) and neuraminidase (NA or N). There are 14 known H subtypes and 9 known N subtypes. The present invention extends to all subtypes, serotypes and serogroups of infections diseases, such as influenza and meningitis.

In embodiments where the antigenic peptide fragment can be derived from a protozoan pathogen, the protozoa may typically be an intracellular protozoan, such as *leishmania* or *trypanosoma.*

In embodiments where the antigenic peptide fragment can be derived from a yeast or fungi, said fungi may be derived from a genus selected from the group comprising: *Acremonium, Alternaria, Amylomyces, Arthoderma, Aspergillus, Aureobasidium, Blastochizomyces, Botrytis, Candida, Cladosporium, Crytococcus, Dictyostelium, Emmonsia, Fusarium, Geomyces, Geotrichum, Microsporum, Neurospora, Paecilomyces, Penicillium, Pilaira, Pityrosporum, Rhizopus, Rhodotorula, Saccharomyces, Stachybotrys, Trichophyton, Trichoporon*, or *Yarrowia.*

In certain embodiments, the antigenic peptide fragment may be derived from a tumour cell. In such embodiments, typically the antigenic peptide fragment is, or is a fragment of, a tumour specific antigen. In certain embodiments the tumour cell may be derived from a cancerous or malignant condition selected from the group including Acute and Chronic Myelogenous Leukemia (AML, CML), Follicular Non-Hodgkins lymphoma, malignant melanoma, Hairy Cell leukaemia, multiple myeloma, carcinoid tumours with carcinoid syndrome and liver and lymph node metastases, AIDS related Kaposi's sarcoma, renal cell carcinoma, adenocarcinoma of the large bowel, squamous cell carcinoma of the head and neck. Furthermore, it would be well known to the person skilled in the art that some infectious diseases can cause cancer in subjects who they infect. Accordingly, administration of a complex of the invention wherein the polypeptide is derived from an infectious disease can be used to treat or prevent cancer. For example, a complex comprising a polypeptide derived from human papillomavirus can be used to treat or prevent cancer, such as cervical cancer in a suitable subject.

In certain embodiments, the polypeptide which is present in the isolated and purified complexes of the invention confers heterologous protection to a subject who is administered said complexes, for example, as the immunogenic determinant in a vaccine composition. Such heterologous protection may typically result from a polypeptide which is derived from one strain of a pathogen, such as a bacteria, mediating an immune response in the vaccinated subject which provides protective immunity against at least one other strain of the same pathogen. Such heterologous protection may therefore provide broad immunological protection against a pathogen, or derivatives thereof.

In one specific heterologous protection may typically result from a polypeptide which is derived from a non-pathogenic strain, such as an attenuated bacteria, mediating an immune response in the vaccinated subject which provides protective immunity against at least one other pathogenic strain of that organism. Such heterologous protection may therefore provide broad immunological protection against a pathogen, or derivatives thereof.

In one specific embodiment, a complex comprising a polypeptide which confers such heterologous protection may be used to confer protection against several strains of a disease, such as meningitis A, B and C. In such an embodiment, a polypeptide derived from a strain of, for example, meningitis B, such as MC58, can confer protective immunity not only against cross serotype strains of meningitis B, but also cross serotype strains of meningitis A and C.

In certain further embodiments, the antigenic peptide fragment is expressed in a host cell by recombinant means, for example, by introduction into the host cell in a vector or similar construct.

In certain further embodiments, the host cell may be a eukaryotic cell which is infected by an intracellular pathogen. In such embodiments, the stress protein complex may comprise a heat shock protein derived from the host cell complexed to an antigenic peptide fragment derived from the intracellular pathogen.

In certain embodiments of the invention, the source mixture is a cell lysate which is produced from a cell population which has been exposed to a stress inducing stimuli which is suitable to cause the induction of the expression of stress proteins, such as heat shock proteins. In certain embodiments, the stress inducing stimuli is selected from the group comprising, but not limited to: heat shock, osmotic shock, pressure and nutrient deprivation. In certain other embodiments, the stress induction is achieved by the genetic modification of a cell to cause the constitutive expression of a heat shock protein gene. In one such embodiment the genetic modification is the inactivation of repressor genes that suppress the expression of stress proteins such as the hspR and HrcA repressor genes in microbial pathogens. Other such genetic modifications are described in PCT publication No. WO 2002/020045 and citations referred to therein.

For the non-genetic induction of stress proteins, the optimum conditions for inducing the stress proteins can readily be determined by simple trial and error with the effect of a change of stress stimuli being assessed with regard to levels of stress protein production using conventional techniques, such as those described in Current Protocols in Immunology, Wiley Interscience, 1997. Other such conditions are described in PCT Publication No. WO 2001/013944 and the citations referred to therein.

In one embodiment, at least one heat shock protein/antigenic peptide complex (HspC) enriched preparations (HEP) which is purified using the methods of the present invention comprise heat shock protein/antigenic peptide fragment complexes (HspCs), which include, but which are not limited to hspC65, hspC70, hspC90 and hspC100.

Ion Exchange Conditions

The method of the invention is based on separating proteins using a methodology based on ion exchange chromatography. However, the method has been improved over standard ion exchange chromatography protocols and procedures currently used in the art in order to remove chemicals which may adversely affect protein structure and integrity, or which may result in contaminants being present in the purified fractions.

Ion exchange chromatography relies on charge-charge interactions between proteins present in the source mixture and the charges provided by an immobilized resin or matrix. Ion exchange chromatography may take the form of cation exchange chromatography, in which positively charged ions bind to a negatively charged resin, or anion exchange chromatography, in which the protein binding ions are negative, and the immobilized functional matrix or resin has a positive charge. Once the stress protein complexes present in the source mixture are bound to the ion exchange resin or matrix, the resin or matrix is washed to equilibrate the resin or matrix with a starting buffer. Typically this buffer is of low ionic strength. The method of the present invention provides that the bound stress protein complexes are then eluted off in fractions by providing a buffer with a different ionic character to the resin or matrix. The changing of the properties or concentration of the buffer alters the binding strength of the stress protein complexes which are bound to the resin or matrix. In particular embodiments, the buffer is varied to provide varying ionic characters or conditions. This difference in ionic character can be achieved by providing an increasing salt gradient to the resin or matrix, typically through the use of a second buffer, such as sodium chloride or a sodium chloride based solution. The eluted fractions of the buffer over the increasing salt gradient can be collected in appropriate fractions, with the fractions eluted at different pI's containing different protein complexes. As the pI (isoelectric point) of the desired protein complexes has been identified, the eluted fraction containing the complexes of interest will be readily identifiable. Techniques such as absorbance at 280 nm can also be used to identify the elution of protein fractions and these fractions can be tested to identify the fractions which contain purified stress protein complex.

The isoelectric point (pI) is the pH at which a particular molecule, such as the protein complexes of the invention, has no net electrical charge. The pI value of a protein complex can be determined from its primary sequence or empirically using conventional isoelectric focussing techniques and commercially available equipment. The pI value of the protein can be used to affect the solubility of the protein at a particular pH. Protein molecules contain both acidic and basic functional groups. Further, amino acids may be positive, negative or neutral in charge. These factors give a protein its overall charge. At a pH lower than their pI, proteins carry a net positive charge. At a pH above their pI, proteins carry a net negative charge. Proteins have minimum solubility in salt solutions at which the pH which corresponds to their pI. This can lead to the protein complex precipitating out of solution. It is therefore desirable that when varying the salt gradient in accordance with the method of the invention, that the pH is not lowered from the initial pH as this may result in the protein complexes precipitating out of solution. Typically therefore, once the pH is set, it is not increased. In certain embodiments, the increase of the salt gradient results in an increase in pH.

Conventionally, ion exchange chromatography has been used to separate individual proteins for their purification. For example U.S. Pat. Nos. 5,750,119 and 5,997,873 use MonoQ columns to purify hsp70, hsp90 and grp96, while the same heat shock proteins have also been individually purified using DEAE chromatography (Menoret (2004) Methods 32:7-12 and Zabrecky and Sawlivich (2004) Methods 32:3-6. MonoQ chromatography. The method of the present invention is used for the isolation and purification of mixtures of stress protein complexes and the term “purified stress protein complex” as used herein refers to chaperone preparations where purification results in reduction of at least about 40 to about 75% in other cellular contaminants from the proteome.

As such, in certain embodiments, the method comprises varying the salt concentration of a buffer used in combination with the matrix or resin, for example by using a buffer such as sodium chloride. Typically this variation in the salt gradient of the buffer causes the stress protein complexes to be eluted, typically in fractions consistent with changes in the salt concentration. Accordingly, in certain embodiments, the elution buffer provides a salt gradient. More preferably the elution buffer contains sodium chloride (NaCl). In certain embodiments, the salt gradient is varied by varying the presence of sodium chloride (NaCl) in the elution buffer to which the matrix is exposed. In certain embodiments, the progressive addition of the elution buffer provides a pH gradient. Typically, this can be varied as the constituents of the buffer are varied. In certain embodiments, the elution buffer comprises sodium chloride at a concentration of from about 50 mM to about 500 mM. In certain embodiments, the pH of the elution buffer is from about pH3 to about pH10.

In certain embodiments, the stress protein complexes are present in fractions collected from the ion exchange chromatography step of the invention, wherein said fractions which are eluted have a pI in the range of 4 to 8. In certain embodiments, the stress protein-polypeptide complexes are eluted in the fractions which are eluted at a pI of 4.5 to 6.5. In certain embodiments, the pI of the stress protein complexes which are to be purified may be firstly determined by isoelectric focussing.

In certain embodiments, the purification methodology is not performed in the presence of (i.e. in the absence of) urea or a similar compound or solution within the buffer. In certain embodiments, ampholytes are not used in the purification methodology, and in particular are not present in the buffer.

Typically the method comprises the steps of applying the source mixture to an ion exchange matrix, wherein the ion exchange matrix can be provided in a column adjusting the pH, varying the salt gradient across the ion exchange matrix, and collecting the eluted fractions, said fractions comprising purified or enriched stress protein complexes, the elution of which is caused by the changing of the salt gradient under specific conditions. In certain embodiments, the matrix is a resin. In further embodiments, the matrix is a membrane. Typically the matrix is comprised of charged particles.

In certain embodiments, the ion exchange is performed using an ion exchange membrane absorber which serves to separate complex protein mixtures into basic and acidic fractions. The inventors have identified that such an embodiment of ion exchange results in a method which is convenient, fast and reproducible and therefore can produce a consistently high yield of stress protein complexes, as would be required for the production of commercial quantities of a vaccine composition which comprises a protein complex component, such as a stress protein-peptide complex as the immunogenic determinant.

In one embodiment, the heat shock protein/antigenic peptide complex (HspC) enriched preparations (HEP) can be eluted from the ion exchange chromatography medium using any suitable elution buffer known to the skilled person in order to maintain protein integrity.

The terms "ion-exchange" and "ion-exchange chromatography" refer to a chromatographic process in which an ionizable solute of interest (e.g., a protein of interest in a source mixture) interacts with an oppositely charged ligand linked or provided to a solid phase ion exchange material under appropriate conditions of pH and conductivity, such that the solute of interest interacts non-specifically with the charged ligand more or less than the solute impurities or contaminants in the mixture. The contaminating solutes in the mixture can be washed from the charged ligand linked to the ion exchange material or are bound to or excluded from the material, faster or slower than the solute of interest. "Ion-exchange chromatography" specifically includes cation exchange, anion exchange, and mixed mode chromatographies.

In certain embodiments, the ion exchange chromatography medium includes an ion exchange column. Typically, the ion exchange column includes a high flow base, such as an agarose or sepharose high flow base. Optionally the high flow base includes a surface extender, such as animal free dextran. Suitable ion exchange media include both cation and anion exchange resins and columns including those derivatized with quaternary ammonium salts and sulphonic moieties, for examples the CaptoQ™ column and CaptoS™ resins (GE Healthcare Limited).

In certain embodiments, the source material, for example the cell lysate is buffer exchanged into 50 mM phosphate buffer pH6.8. In certain embodiments, the ion exchange column includes a high flow base, preferably an agarose high flow base. In certain embodiments, the high flow base includes a surface extender, e.g. animal free dextran, and a Q ligand, e.g. a quaternary ammonium salt.

The phrase "ion exchange material" refers to a solid phase that is negatively charged (i.e. a cation exchange resin) or positively charged (i.e. an anion exchange resin). In one embodiment, the charge can be provided by attaching one or more charged ligands (or adsorbents) to the solid phase, e.g. by covalent linking. Alternatively, or in addition, the charge can be an inherent property of the solid phase (e.g. as is the case for silica, which has an overall negative charge).

In certain embodiments, where the ion exchange chromatography is cation exchange chromatography, the cation exchange chromatography step employs a ligand selected from the group comprising, but not limited to: sulfonate, carboxylic, carboxymethyl sulfonic acid, sulfoisobutyl, sulfoethyl, carboxyl, sulphopropyl, sulphonyl, sulphoxyethyl and orthophosphate.

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies); a sulfoethyl based group (e.g., Fractogel SE from EMD, or Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., Fractogel EMD SO3 from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrex Cellufine C500 and C200 from Millipore, CM52, CM32, CM23 and Express-Ion C from Whatman, Toyopearl CM-650S, CM-650M and CM-650C from Tosoh); sulfonic and carboxylic acid based groups (e.g. BAKERBOND Carboxy-Sulfon from J. T. Baker); a carboxylic acid based group (e.g., WP CBX from J. T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO—from EMD); a sulfonic acid based group (e.g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., pI 1 from Whatman).

If desirable, a cation exchange membrane can be used instead of a cation exchange resin, for example, Sartobind S (Sartorius; Edgewood, N.Y.).

In certain embodiments, where the ion exchange chromatography is anion exchange chromatography, the anion exchange chromatography step may employ a ligand selected from the group consisting of: quaternary ammonium or amine, dethylamine, diethylaminopropyl, amino, timethylammoniumethyl, trimethylbenzyl ammonium, dimethylethanolbenzyl ammonium, polyamine.

An "anion exchange resin" refers to a solid phase which is positively charged, thus having one or more positively charged ligands attached thereto. Any positively charged ligand attached to a solid phase suitable to form the anionic exchange resin can be used, such as quaternary amino groups. For example, a ligand used in AEC can be a quaternary ammonium, such as quaternary alkylamine and quaternary alkylalkanol amine, or amine, diethylamine, diethylaminopropyl, amino, timethylammoniumethyl, trimethylbenzyl ammonium, dimethylethanolbenzyl ammonium, and polyamine. Alternatively, for AEC, a membrane having a positively charged ligand, such as a ligand described above, can be used instead of an anion exchange resin.

Commercially available anion exchange resins include, but are not limited to, DEAE cellulose, Poros PI 20, PI 50, HQ 10, HQ 20, HQ 50, D 50 from Applied Biosystems, MonoQ, MiniQ, Source 15Q and 3OQ, Q, DEAE and ANX Sepharose Fast Flow, Q Sepharose high Performance, QAE SEPHADEX™ and FAST Q SEPHAROSE™ from GE Healthcare, WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Q HyperZ, Trisacryl M and LS DEAE, Spherodex LS DEAE, QMA Spherosil LS, QMA Spherosil M from Pall Technologies, DOWEX Fine Mesh Strong Base Type I and Type II Anion Resins and DOWEX MONOSPHER E 77, weak base anion from Dow Liquid Separations, Matrex Cellufine A200, A500, Q500, and Q800 from Millipore, Fractogel EMD $TMAE_3$ Fractogel EMD DEAE and Fractogel EMD DMAE from EMD, Amberlite weak and strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and $650C_3$ QAE-550C and 650S, DEAE-65OM and 650C from Tosoh, and QA52, DE23, DE32, DE51, DE52, DE53, Express-Ion D and Q from Whatman.

If desirable, an anion exchange membrane can be used instead of an anion exchange resin. Commercially available anion exchange membranes include, but are not limited to, Sartobind Q from Sartorius, Mustang Q from Pall Technologies and Intercept Q membrane from Millipore.

In certain embodiments, the anion exchange chromatography is performed at a pH of from about 5.0 to about 9.0 and at a conductivity of from about 0.5 to about 5 mS/cm.

In certain embodiments, wherein the cation exchange chromatography is performed at a pH of from about 4.0 to about 9.0 and at a conductivity of from about 0.5 to about 15 mS/cm.

The “pI” or “isoelectric point” of a polypeptide refers to the pH at which the polypeptide’s positive charge balances its negative charge. The pI can be calculated according to various conventional methodologies, e.g., from the net charge of the amino acid and/or sialic acid residues on the polypeptide or determined empirically using isoelectric focussing techniques.

The term “elution buffer”, as used herein, refers to a buffer used to elute the protein of interest from the resin. The pH and conductivity of the elution buffer are selected such that the protein of interest is eluted from the CEO resin used in the process. Examples of buffers suitable for use as an elution buffer may include a phosphate or TRIS based buffer.

In certain embodiments, the elution buffer is sodium chloride (NaCl) which may be used at a concentration of about 50 mM to 500 mM.

The pH of the elution buffer can be from about 3 to about 10, more preferably pH from about 4 to about 9. In certain embodiments, the pH of the buffer is about 6.8.

The present invention further extends to HspC-enriched lysates (HEL) which are purified according to the methods of the present invention. Said HspC-enriched lysate may also be known as an HspC-enriched fraction (HEF) or an HspC enriched composition (HEC). Accordingly, a further aspect of the present invention provides at least one HspC-enriched lysate purified by the method of the foregoing aspect of the invention for use in the preparation of a vaccine composition. Typically the HspC-enriched lysate is derived from at least one eluted fraction obtained from the ion exchange method of the present invention.

In certain embodiments, the HspC-enriched lysate comprises a complex formed between a stress protein (heat shock protein) which is complexed with a polypeptide or a peptide fragment, in particular and antigenic peptide fragment. In certain embodiments, the purified HspC-enriched lysate is derived from a microbial host, pathogen, eukaryotic host, cell infected with a pathogen, or a malignant or a cancerous cell. In a preferred embodiment, the purified complex is a stress protein/peptide complex wherein the stress protein is selected from the group consisting of hsp65, hsp70, hsp90 and hsp100.

The invention further extends to vaccine compositions which comprise the purified HspC-enriched lysates produced according to methods of the invention. Said vaccine compositions are typically administered to mammalian subjects, in particular humans. However, due to the acknowledged high level of homology between stress proteins from different species, vaccine compositions may be used to vaccinate a wide variety of subjects, typically animals and preferably humans, in order to confer long term protective immunity in said subject.

As such, further aspects of the invention provide a vaccine composition comprising a purified heat shock protein-polypeptide complex enriched eluate fraction or lysate obtained by the method of the first aspect of the invention. Various further aspects of the present invention extend to the use of isolated purified heart shock protein-polypeptide complexes obtained by the methods of the invention in a vaccine composition for use in mediating an immune response in a subject against the pathogen or cancerous cell from which the polypeptide of the complex is derived.

In a yet further aspect, the present invention extend to a vaccine composition comprising at least one heat shock protein-polypeptide complex (hspc) as the immunogenic determinant against which an immune response is raised when the vaccine composition is administered to a subject, wherein the heat shock protein-polypeptide complex is produced by a method comprising the steps of:

(i) providing a source mixture comprising at least one target stress protein complex formed from a stress protein complexed to a polypeptide fragment,
(ii) determining the isolelectric point (pI) of the at least one target stress protein complex which is to be purified from the source mixture;
(iii) subjecting the source mixture to purification using ion exchange, wherein the cell lysate is buffered to a pH within 2 units of the pI of the target stress protein complex, and wherein a salt gradient is used to elute the target stress protein complex.

In certain embodiments, the purification method provides for the isolation of a plurality of heat shock protein-peptide complexes (hspcs) from the source mixture. In certain embodiments, the heat shock protein-polypeptide complexes comprise heat shock proteins of the same family, for example heat shock proteins from the HSP70 family. In further embodiments, the heat shock protein-peptide complexes comprise heat shock proteins from different heat shock protein families. Typically it is required that the polypeptide fragment is derived from the infectious pathogen against which immunity is to be induced by the vaccine. In certain embodiments, the polypeptide may result in an immune response being generated wherein such a response mediates protective immunity in a host against a pathogen, and in particular a pathogen which causes an infectious disease. For example, the polypeptide may be derived from a non-pathogenic variant of a pathogen, wherein a polypeptide derived from said non-pathogenic variant mediates a protective immune response in the subject to whom it is administered which provides protective immunity against the pathogen to which the non-pathogenic variant is related. In certain embodiments, the polypeptide is a tumour specific antigen, wherein any immune response raised there against results in protective immunity being mediated in the vaccinated host against a cancer cell expressing such an antigen. In certain further embodiments, the polypeptide is derived from a pathogen, such as human papillomavirus, wherein said pathogen can cause cancer in a host infected by said pathogen.

In certain further embodiments, the vaccine composition comprises a polypeptide which is derived from a pathogenic organism and which mediates a heterologous immune response, said heterologous immune response resulting in protective immunity being mediated not only against that pathogen, but other strains related to that pathogen.

In certain yet further embodiments, the vaccine composition comprises a polypeptide which is derived from a non-pathogenic organism and which mediates a heterologous immune response, said heterologous immune response resulting in protective immunity being mediated not only against that non-pathogen, but other pathogenic strains related to that organism.

In certain embodiments, the vaccine composition may further comprise, or be administered along with at least one adjuvant. In certain embodiments, the adjuvant is selected from the group consisting of, but not limited to; Freund's complete adjuvant, Freund's incomplete adjuvant, Quil A, Detox, ISCOMs and squalene. Further suitable adjuvants include molecules that target receptors which mediate innate immune responses such as Toll-like receptors, NODs, NALPs and RIGs.

In certain embodiments, the vaccine composition is suitable for administration to a subject by injection. The injection method can be needleless or may use a needle which, for example penetrates the dermis of a human subject. In certain further embodiments the vaccine is suitable for oral administration, or can be administered transdermally, or by pulmonary delivery.

In certain embodiments, the purified and isolated heat shock protein-polypeptide fragments or the vaccine compositions containing the same are administered as a prophylactic vaccine. In certain further embodiments, the purified and isolated heat shock protein-polypeptide fragments are administered as a therapeutic vaccine.

In various further aspects, the present invention extends to the use of the purified heat shock protein-polypeptide fragments, or to vaccine compositions containing the same are administered as a booster vaccine to enhance the immune response generated in a host to a pathogen or cancer antigen to which the subject has previously been exposed to, typically by way of infection or a previously administered vaccine.

In certain further aspects the present invention provides for the use of stress protein-peptide complexes which have been purified using the methods of the invention in the preparation of a medicament for the treatment of an infectious disease or a cancerous or a malignant condition. Typically the infectious disease or cancerous condition is the same as that from which the polypeptide of the complex is derived from. In certain embodiments, the purified stress protein-peptide complexes may be isolated.

In certain further aspects, the present invention provides a stress protein-peptide complex which has been purified by the method of the first aspect of the present invention for use as the immunogenic determinant in a vaccine composition for use in treating or preventing the infection of a subject with an infectious disease. Typically the infectious disease or cancerous condition is the same as that from which the polypeptide of the complex is derived from. In certain embodiments, the purified stress protein-peptide complexes may be isolated.

In certain further aspects, the present invention provides a stress protein-peptide complex which has been purified by the method of the first aspect of the present invention for use as the immunogenic determinant in a vaccine composition for use in treating or preventing the occurrence of a cancerous or a malignant condition in a subject. Typically the malignant or cancerous condition is the same as that from which the polypeptide of the complex is derived from. In certain embodiments, the purified stress protein-peptide complexes may be isolated.

A yet further aspect of the invention provides a vaccine composition comprising an isolated stress protein-polypeptide complex which has been purified in accordance with a method of the present invention in the preparation of a medicament for use in the treatment of an infectious disease. Typically the infectious disease is the same as that from which the polypeptide of the complex is derived from. In certain embodiments, the infectious disease is tuberculosis or meningitis.

In certain further aspects, the present invention extends to a vaccine composition comprising an isolated stress protein-polypeptide complex which has been purified in accordance with a method of the present invention for use in treating or preventing an infectious disease in a subject. Typically the infectious disease is the same as that from which the polypeptide of the complex is derived from. In certain embodiments, the infectious disease is tuberculosis or meningitis.

The invention further provides for the use of the purified heat shock protein-polypeptide complex-enriched lysates of the invention in a method of vaccinating a subject to induce immunity against a pathogen derived infectious disease or cancerous or malignant condition.

Accordingly a yet further aspect of the invention provides for a method of vaccinating a subject against a pathogen derived infectious disease or a cancerous condition, said method comprising the steps of:

- providing a vaccine composition comprising a purified heat shock protein-polypeptide-enriched preparation obtained according to the method of the present invention, said purified HspC-enriched preparation being derived from a cancerous cell, an infected cell or a pathogen against which protective immunity is desired, and
- administering a vaccine composition comprising the HspC-enriched preparation to a subject in an amount sufficient to elicit an immune response in the subject against the HspC-enriched preparation.

As used herein, the term "vaccine composition" means any composition containing an immunogenic determinant which stimulates the immune system in a manner such that it can better respond to subsequent challenges or pathogenic infections. It will be appreciated that a vaccine usually contains an immunogenic determinant and an adjuvant, the adjuvant serving to non-specifically enhance the immune response to the immunogenic determinant.

In certain embodiments, the subject is an animal, typically a human. The methods of the invention can also be used to purify protein complexes for use in a vaccine composition for the treatment of other animals such as horses, cattle, goats, sheep, swine and birds.

In certain embodiments, the microbial pathogen from which the purified HspC-enriched preparations of the invention are derived, may be selected on the grounds that it causes disease or infection, or if a polypeptide derived therefrom is administered to a subject, that said polypeptide will result in protective immunity being generated in the host against a pathogen organism which causes an infectious disease. The vaccine compositions provided by the invention may be used either prophylactically or therapeutically. The inventors however recognise that the compositions may be particularly useful as prophylactic vaccines due to their economy of production and their ability to elicit a protective immune response.

The inventors have further surprisingly identified that stress protein-peptide complexes which are obtained using the methods of the invention can be used as "booster" vaccinations, said booster vaccinations enhancing the immunity provided in a subject against a pathogen or a cancerous condition, wherein the initial immunity was conferred by vaccination with a live or attenuated vaccine, or by a vaccine composition wherein the immunogenic determinant was a stress protein-peptide complex.

Accordingly, a yet further aspect of the invention provides for a method of boosting a protective immune response in a subject against a pathogen derived infectious disease or a cancerous condition, wherein said protective immune response has been elicited by the previous administration of a live or attenuated vaccine or of a stress protein-peptide complex comprising a peptide derived from the pathogen against which immunity is desired, said method comprising the steps of:

- providing a composition comprising a purified HspC-enriched preparation obtained according to the method of the present invention, said purified HspC-enriched preparation being derived from a cancerous cell, a pathogen infected cell or a pathogen against which protective immunity is desired, and
- administering a composition comprising the HspC-enriched preparation to a subject in an amount sufficient to elicit an immune response in the subject against the HspC-enriched preparation.

In certain further embodiments, the HspC containing vaccine compositions of the present invention provides compositions for the boosting of immune responses in animals that have been previously immunised with other subunit, multi-subunit, carbohydrate or conjugate vaccines. In yet further embodiments, the HspC vaccines of the present invention provides compositions for the boosting of immune responses in animals that have been previously immunised with nucleic acid or live vaccines. In yet further embodiments, the HspC containing vaccine compositions of the present invention provide for the boosting of immune responses mediated in subjects that have been previously infected with or immunised against a pathogen or cancer specific antigen.

In certain further aspects, the present invention extends to vaccine compositions comprising the stress protein-peptide complexes purified by the invention for use in the boosting of immune responses in animals, wherein the animal has previously been vaccinated with a vaccine composition comprising at least one pathogen derived antigen, a pathogen, in particular an attenuated pathogen, or a cancer specific antigen. Typically the peptide component is derived from the same pathogen or cancerous cell, as that which provided the immunogenic determinant for the initial vaccination In certain further embodiments, the present invention provides compositions for the preparation of cellular vaccines such as dendritic cells (DCs) which have been pulsed with the purified HspC-enriched preparations of the invention. Administration of such pulsed dendritic cells to subject will result in a T-cell mediated response being directed against the stress protein/antigenic cell complex. Such a therapy can be particularly effective when treating a subject with a cancerous or malignant condition. In such embodiments, typically the stress protein/peptide complex is derived from a cancerous cell.

A yet further aspect of the invention provides a kit comprising an ion exchange matrix, an elution buffer not containing a chaotrope, ampholytes or a surfactant and instructions for recovering heat shock protein-polypeptide complexes.

A yet further aspect of the invention provides an elution buffer for the elution of stress protein-peptide fragment complexes from an ion exchange solid phase, wherein the elution buffer does not contain a chaotrope, an ampholyte or a surfactant.

DETAILED DESCRIPTION OF THE INVENTION

Figure 1:
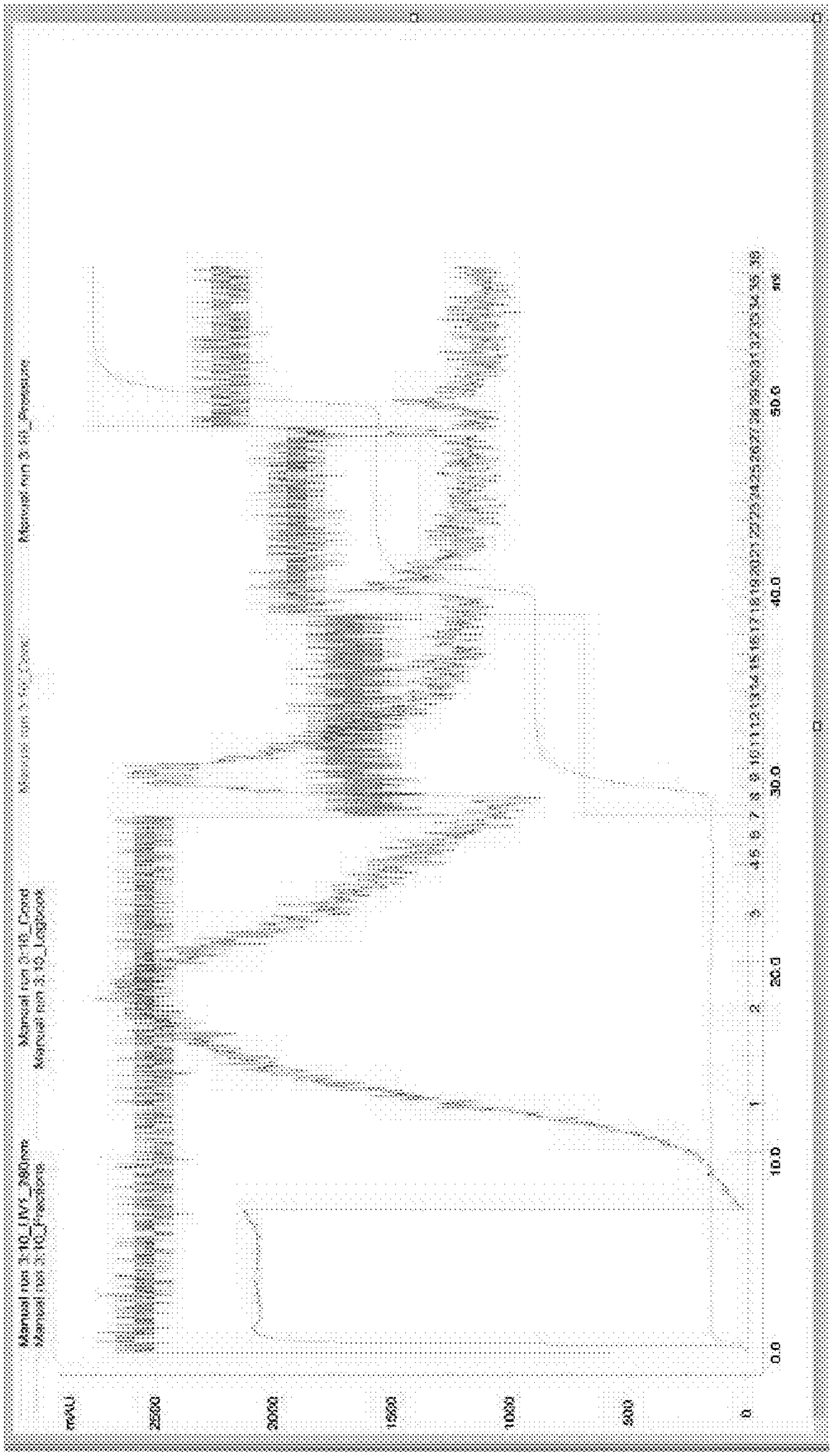
FIG. 1 shows the SDS-PAGE analysis of the purification of protein complexes from BCG bacterial cell lysates and the analysis of these samples for the major DnaK and GroEL heat shock protein families (Hsp71 and Hsp 65) and Ag85 by Western blotting, showing clear purification of the HEPs from other major BCG antigens such as Ag85.

The present invention provides an improved method for the purification of complexes, comprising a stress protein complexed to a peptide or peptide fragment, from a source mixture, typically a cell lysate. In particular, the invention provides for the recovery of complexes comprised of heat shock proteins complexed to polypeptides from a sample source. The invention is based upon the use of net charge of protein complexes to elute desired complexes within specific fractions from an ion exchange matrix in order to recover a fraction which comprises the desired heat shock protein-polypeptide complexes. Accordingly, the method of the present invention allows for the recovery of a fraction which comprises a purified fraction which is enriched with stress protein-polypeptide complexes. The method of the present invention further provides for the recovery of heat shock proteins of different families, such as hsp40, hsp60, hsp70, hsp90, gp96 from single sample.

Said recovered complexes, or the fraction containing the same can be used as the immunogenic determinant in vaccine compositions for the treatment of infectious diseases. The methods of the invention have the advantage that complexes comprising different polypeptides derived from a common pathogen can be present in the recovered fractions or complexes. When administered as the immunogenic determinant of a vaccine composition, a heterologous immune response which mediates long term protective immunity which is not serotype specific or serogroup specific in relation to other pathogens related to the pathogen from which the polypeptides of the complex are derived, can result.

The improved method of the invention provides for protein complexes to be purified using ion exchange based methods, without the need to use chemicals such as chaotropes, surfactants and ampholytes (ampholines) in the purification methodology. Such a method is advantageous as the presence of extraneous ingredients in pharmaceutical preparations is generally undesirable. Hence, the purified complexes obtained using the method of the invention can be used to produce improved vaccine preparations.

The method of the invention is further advantageous in that it provides a purification method which has a greater capacity than previously used techniques, such as isoelectic focusing for the purification of stress protein complexes, such that cost effective production of vaccines containing such complexes can be achieved.

Furthermore, the inventors have surprisingly identified that stress protein complexes which are purified using the methods of the invention are more immunogenic than similar complexes obtained using purification techniques such as isoelectric focusing (IEF). Hence, the HspC complexes obtained by the methods of the invention are more immunogenic than those purified using standard purification methods known in the art.

Ion Exchange Chromatography (IEC) relies on charge-charge interactions between the proteins in the sample and the charges immobilized on the resin of choice. In general IEC can be subdivided into cation exchange chromatography or anion exchange chromatography. For example CaptoQ™ (a positively charged anion exchanger) may be utilised when the target protein complex is predicted to be negatively charged at pH6.8 (see table 1) and CaptoS™ (a negatively charged anion exchanger) may be utilised when the target protein complex is predicted to be positively charged at pH6.8.

TABLE 1

Predicted binding of Hsps to CaptoQ column

| Protein | MW (kDa) | pI | Predicted binding to CaptoQ* |
|---|---|---|---|
| Hsp90 | 75 | 4.7 | strong |
| Hsp71 | 67 | 4.9 | strong |
| Hsp60 (Cpn60.1/ groEL1) | 56 | 4.7 | strong |
| Hsp65 (Cpn60.2/ groEL2) | 57 | 4.6 | strong |
| HspX | 16 | 5 | strong |
| BCG-A (GroES) | 11 | 4.6 | strong |

*phosphate buffer pH 6.8 used for column equilibration

Moreover, the distribution of isoelectric point (pI) of proteins in a proteome is universal for all prokaryotes and can be represented as a bimodal distribution or "butterfly effect" such that approximately 60% of the proteins have a pI≤7 and 40% of the proteome has a pI≥8 (see Table 1). For examples where hspCs from mycobacterial cultures are used to generate a cell lysate, it would be expected that at pH 6.8 at least 40% of the mycobacterial contaminating proteome would be readily removed from the purified complex and hence also from vaccine product using CaptoQ™ IEC. The skilled man will readily understand that the methods of the present invention may be performed using any suitable ion exchange medium which is a high performance medium.

Important technical issues to consider when developing a robust protein purification strategy include a short process run time and careful consideration of the buffer composition. The present inventors aimed to purify protein complexes and in doing so to overcome or reduce issues associated with protein degradation, modification or disruption of the proteins complexes during the purification process. Although highly immunogenic HspC enriched vaccines were prepared with free flow isoelectric focusing (FF-IEF) typical run times were 4 hours and it was also necessary maintain protein solubility with urea. This chaotrope has been shown to have destabilizing effects on both macromolecular structure and protein function. Encouragingly, CaptoQ™ due to the chemical stability of the high flow 'protein friendly' matrix results in a shorter run time and offers a greater flexibility of buffer choice. The present inventors have surprisingly reduced the time taken to prepare 3 mg of HspC enriched preparation from 10 mg of starting material to approximately 2 hours, moreover protein solubility was maintained without the need for chaotropes or surfactants. Additionally, protein degradation levels were reduced.

The methods of the present invention have been used to prepare potential vaccines against tuberculosis, meningitis and influenza. The method utilises the isoelectric point of the target proteins and the buffer pH. The vaccine composition may comprise at least 2 two of the major heat shock proteins thought to be important in generating immunity, specifically Hsp60, and Hsp70 families.

The methods of the present invention have the advantage of being scalable and rapid with the possibility of processing liters of lysate to generate kg amounts of purified protein complex and vaccine composition.

Administration

The vaccine compositions of the present invention may be administered alone but will preferably be administered as a pharmaceutical composition which will generally comprise a suitable pharmaceutically acceptable excipient, diluent or carrier selected depending on the intended route of administration. Examples of suitable pharmaceutical carriers include; water, glycerol, ethanol and the like.

The complexes or vaccine compositions of the present invention may be administered to a patient in need of treatment via any suitable route. Typically, the composition can be administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The complexes or vaccine compositions may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition of the invention is typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the antibody or binding member in the formulation, as well as the route, site and rate of delivery.

Dosage regimens can include a single administration of the composition, or multiple administrative doses of the composition. The compositions can further be administered sequentially or separately with other therapeutics and medicaments which are used for the treatment of the condition for which the antibody or binding member of the present invention is being administered to treat.

As used herein, the term "treatment" and associated terms such as "treat" and "treating" means the reduction of the progression, severity and/or duration of an infectious disease and/or a cancerous condition or at least one symptom thereof, wherein said reduction or amelioration results from the administration of a complex or vaccine composition of the present invention. The term 'treatment' therefore refers to any regimen that can benefit a subject. The treatment may be in respect of an existing condition or may be prophylactic (preventative treatment). Treatment may include curative, alleviative or prophylactic effects.

References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract an infectious disease or cancerous condition.

DEFINITIONS

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived.

As used herein, the term "therapeutically effective amount" means the amount of an agent, binding compound, small molecule, fusion protein or peptidomimetic of the invention which is required to induce an protective immune response against an infectious disease or cancerous condition. As used herein, the term "prophylactically effective amount" relates to the amount of a composition which is required to prevent the initial onset, progression or recurrence of an infectious disease or cancerous condition. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

The term "isolated", when used in reference to the purified heat shock protein-polypeptide complexes of the invention refers to the state in which said complexes are provided in an isolated and/or purified form, that is they have been separated, isolated or purified from a source mixture and/or their natural environment, and are provided in a substantially pure or homogeneous form. Accordingly, such isolated complexes will be free or substantially free of material with which they may be naturally associated with, such as other polypeptides or nucleic acids with which they are found in their natural environment, or the environment in which they are prepared (e.g. cell culture) when such preparation is by recombinant DNA technology practiced in vitro or in vivo.

EXAMPLES

The present invention will now be described with reference to the following examples which are provided for the purpose of illustration and are not intended to be construed as being limiting on the present invention.

Example 1

Preparation of HspC-Enriched Preparations from BCG Cellular Lysates

BCG cell pellets from mid-log heat shocked cultures were lysed and clarified by centrifugation. Cell pellets were resuspended in sterile PBS containing an EDTA-free protease inhibitor cocktail. Resuspended cells were lysed using sonication, a Beadbeater or passed through an Emulsiflex C5 high pressure homogeniser and collected in a sterile bag. Benzonase (250 U/mL) was added to the lysate. The samples were then homogenised a further two times, the cellular lysate transferred to centrifuge tubes and cell debris removed by centrifugation for 20 minutes at 6000 g. The clarified lysate was collected and centrifuged for a further 60 minutes at 14000 g and the supernatant was removed and referenced as high speed clarified lysates. 10 ml of clarified lysates were desalted and buffer exchanged into 50 mM phosphate buffer pH 6.8. The protein concentration of the sample was determined and an IEC (ion exchange chromatography) HspC enriched preparation was prepared by column chromatography as follows. 10 mg of protein was loaded on to a CaptoQ™ column at a flow rate of 0.5 ml/minute. After extensive washing of the column with 50 mM phosphate buffer, pH 6.8 proteins were batch eluted using increasing concentrations of NaCl (150 mM, 300 mM, 500 mM and 1 M). Eluted fractions containing Hsp70 and Hsp65 were analysed using SDS-PAGE and Western blotting using commercial antisera against DnaK (Hsp70), GroEL (Hsp65) and Ag85. Examples of the HEPs prepared are shown in FIG. 1 showing clear purification of the HEPs from other major BCG antigens such as Ag85.

Example 2

Figure 2:
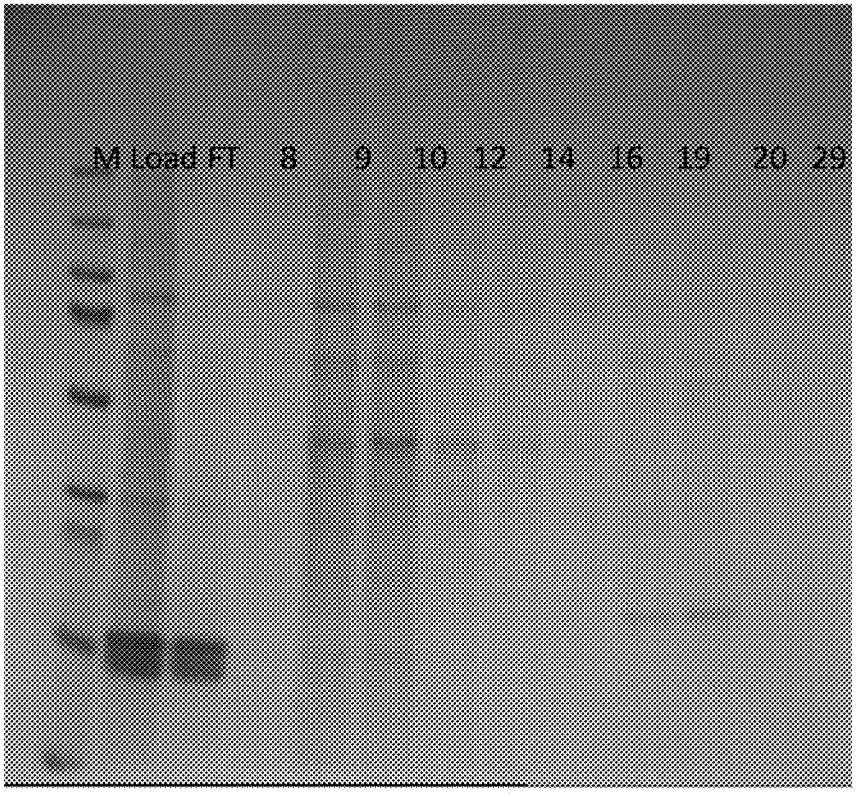
FIG. 2 shows the improved immunogenicity of the HEPs isolated from BCG (IEX) using the method of the invention (IEX) compared to the parent lysate (LSS) and HspCs isolated using conventional isoelectric focussing methods (IEF).
Figure 3:
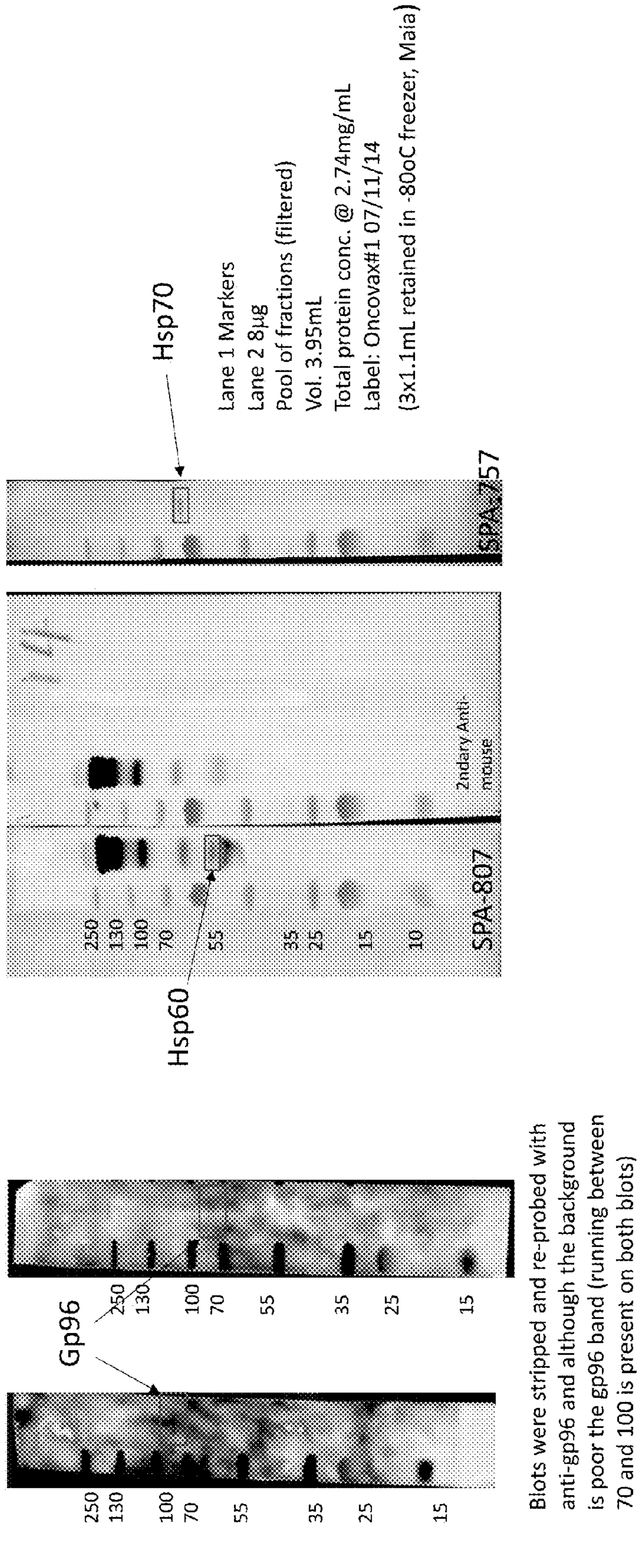
FIG. 3 shows the reduction of lung colony counts in immunised animals challenged with live TB. Animals were immunised with saline as a negative control, live BCG bacteria (BCG) as positive control or primed with live BGC and immunised with HEPs isolated from BCG bacterial cell lysates (IEC single dose and IEC boost).

Immunogenicity of BCG Derived HspC-Enriched Preparations and Induction of a Protective Immune Response Against Live TB Challenge BCG HEPs were used to immunise BalbC mice and spleens harvested from the immunised animals 28 days after immunisation. Spleens were collected into RPMI-1640 and single cell suspensions were made by pressing the spleens through 70 μm cell strainers using a 5 mL syringe plunger into a 50 mL Falcon tube. Cells were counted using trypan blue exclusion on a KOVA glasstic slide haemocytometer and the production of interferon gamma (IFN-γ) assayed in a recall response to TB antigens. $2\times10^6$ splenocytes were added to each well in a 24 well tissue culture plate (Nunc) in 1 mL culture medium and to each well, one of the following antigens was added: BSA (10 μg/ml), Con A (10 μg/ml), TB whole cell lysate (WCL at 50 to 1.56 μg/mL), HEPs, IEF HspCs or Ag85 (10 μg/mL). Culture supernatants from the re-stimulated wells were tested for IFN-γ IL-2, IL-4 and IL-5 using a murine ELISA kit according to the manufacturer's protocol (R&D Systems). FIG. 2 shows typical results obtained with spleen cells from immunised mice re-stimulated with WCL in vitro. The results show that HEPs isolated from BCG (IEC) induced a strong IFN-γ response in the immunised animals, stronger than the parent BCG lysates (LSS) and much stronger than HspCs isolated using conventional free-flow isoelectric focussing method previously described (IEX) for the isolation of multiple HspC families (FIG. 2). Recall responses to WCL were comparable to those seen with Con A and significant but smaller responses were seen against Ag85. The in vitro IFN-γ responses also translated into in vivo protection against live TB challenge in the mouse aerosol challenge model, with a 0.6 log reduction in lung cfu (colony forming units) equivalent or better than the protection observed with live BCG vaccine in this model and the HEPs isolated from BCG were also able to boost BCG primed animals as illustrated by a further reduction in lung cfu (FIG. 3).

Example 3

Preparation of HEPs from *Neisseria meningitidis*

Figure 4:
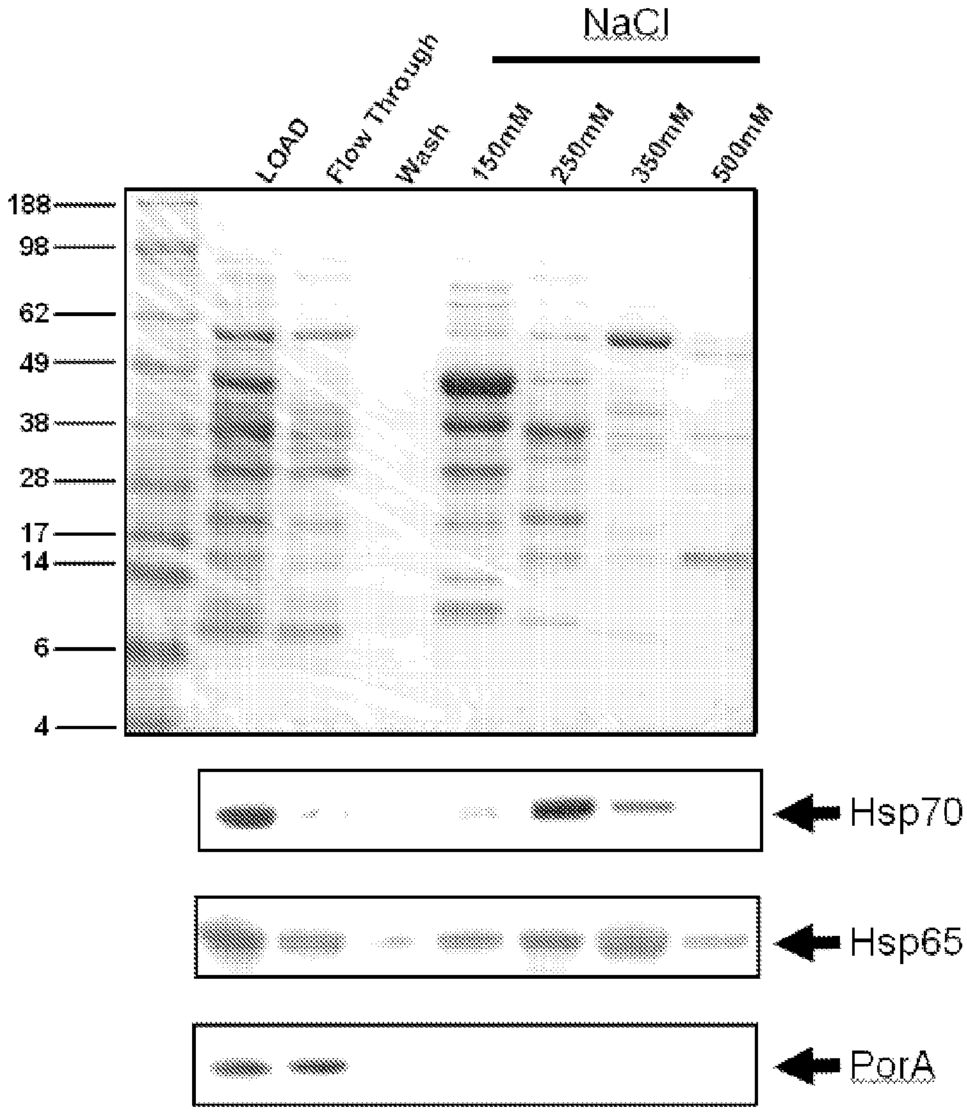
FIG. 4 shows the SDS-PAGE analysis of the purification of protein complexes from *Neisseria meningitidis*, eluted by a step salt gradient (A) and the analysis of these samples for the Hsp70 and Hsp 65 and PorA proteins by Western blotting (B) showing clear purification of the HEPs from other major *N. meningitidis* antigens such as PorA.

Cultures of an acapsulate variant of strain of *Neisseria meningitidis*, MC58 (Mol. Microbiol. 1995, November; 18(4):741-54) were heat shocked at 44° C. and killed by treatment with the antibiotic gentamicin. Cells were processed to produce HEPs as described in Example 1. In brief, cells were lysed by cycles of freezing and thawing or sonication and clarified by centrifugation for 20 minutes at 6,000 g. Clarified extract was loaded onto a column packed with CaptoQ ion exchange resin. After extensive washing of the column with 50 mM phosphate buffer, pH 6.8 proteins were batch eluted using increasing concentrations of NaCl (150 mM, 350 mM, 500 mM). Eluted fractions containing Hsp70 and Hsp65 were analysed using SDS-PAGE (FIG. 4A). Fractions eluted by 150 mM and 300 mM NaCl were combined and dialysed into PBS for use as vaccines. Vaccine composition was assessed by gel electrophoresis and Western blotting for the presence of the major heat shock protein families and the outer membrane porin, PorA. Results are shown in FIG. 4 showing clear purification of the HEPs from other major *N. meningitidis* BCG antigens such as PorA.

Example 4

Figure 5:
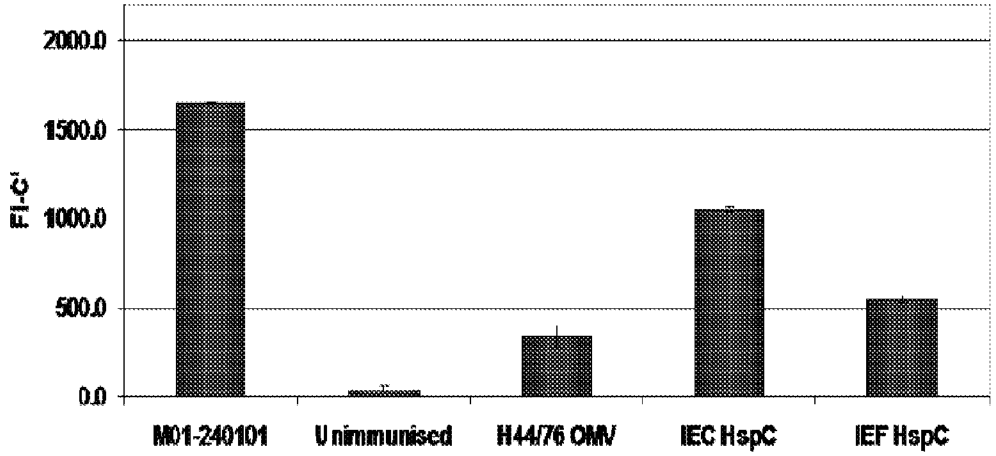
FIG. 5 shows the immunogenicity of the HEPs isolated from *Neisseria meningitidis* using the method of the invention (IEC HspC) compared to the HEPs isolated from *Neisseria meningitidis* using conventional isoelectric focussing methods (IEF HspC). Though both HspCs showed significantly better oposonisation activity against heterologous strains than the current outer membrane vesicle vaccine (H44/76OMV), the IEC HspCs showed much better cross-strain immunogenicity than the IEF HspCs.
Figure 6:
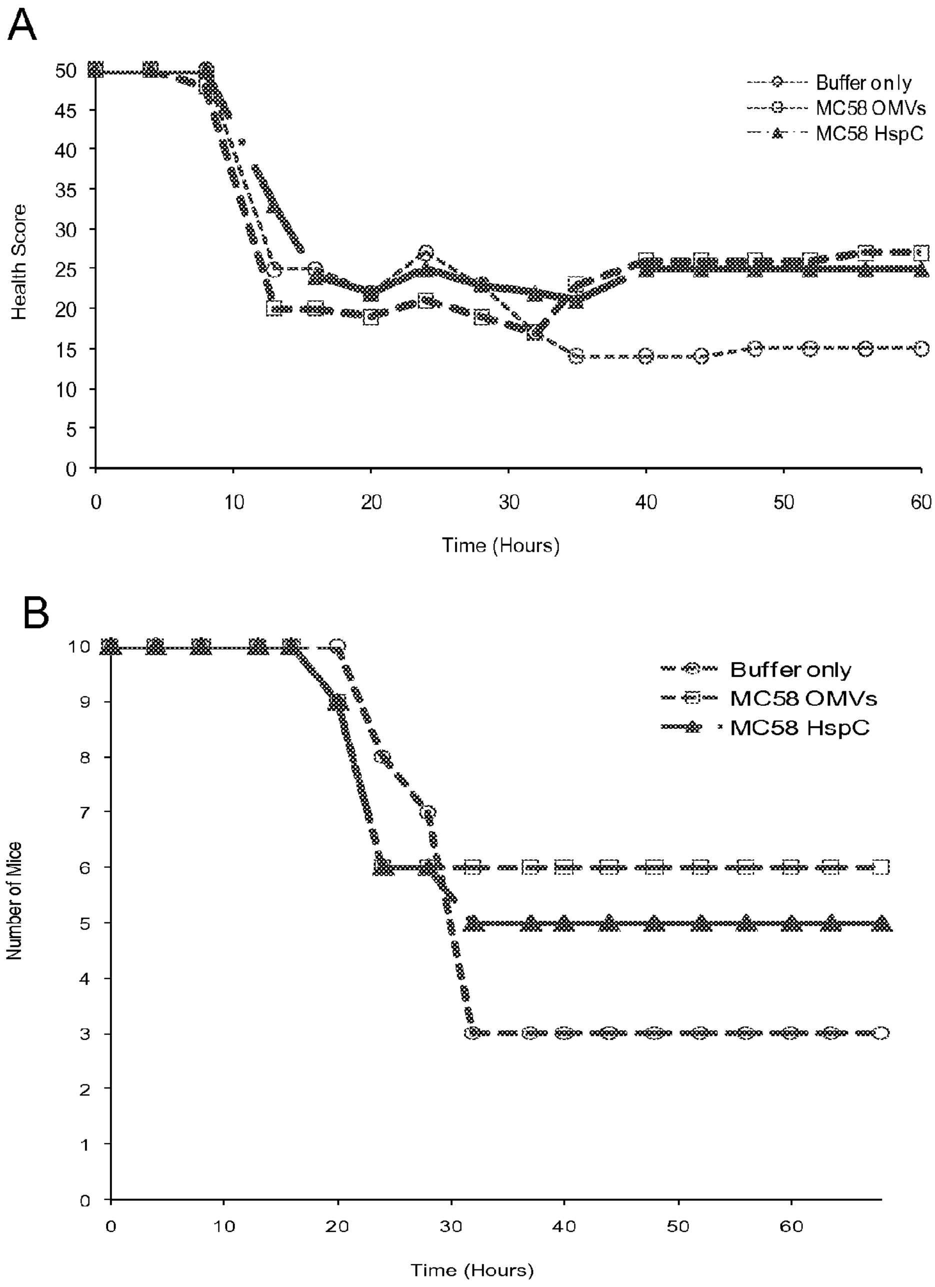
FIG. 6 shows the protective immunogenicity of the HEPs isolated from *N. meningitidis* (MC58 HspC) compared to the conventional outer membrane vesicle vaccine (OMV) in a mouse lethal challenge model demonstrating that the hspC containing vaccine shows equivalence to the current OMV vaccine in both health scores (A) and survival (B) against live challenge with the homologous strain of *N. meningitidis.*
Figure 7:
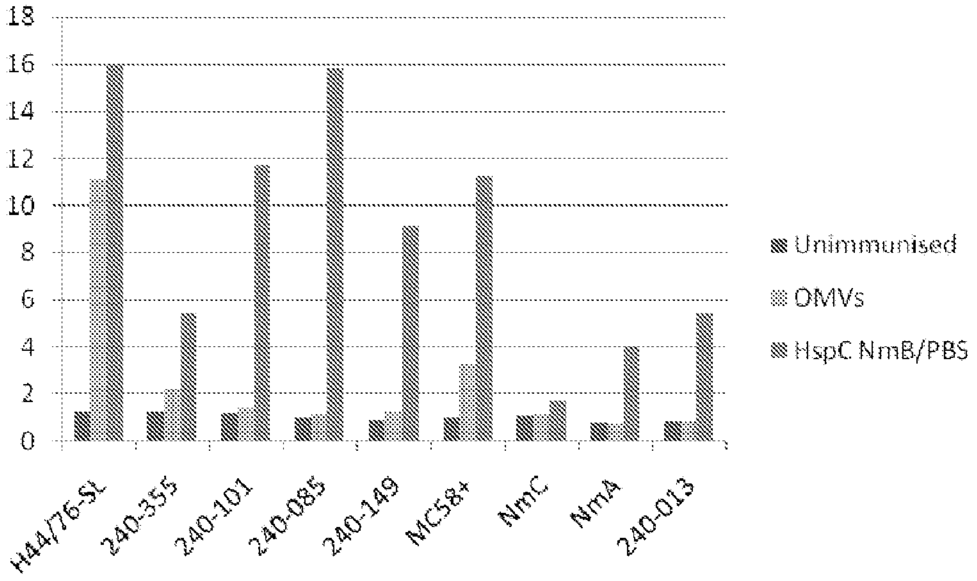
FIG. 7 shows the immunogenicity of the HEPs isolated from *N. meningitidis* B serotype which demonstrates not only good cross serotype reactivity but also significant cross serogroup immunogenicity against Meningitis A (NmA) and Meningitis C (NmC) strains. Protective immunogenicity as assessed by opsonisation activity was significantly better than that seen with the currently clinically used OMV vaccines which show no cross serogroup immunogenicity.
Figure 8:
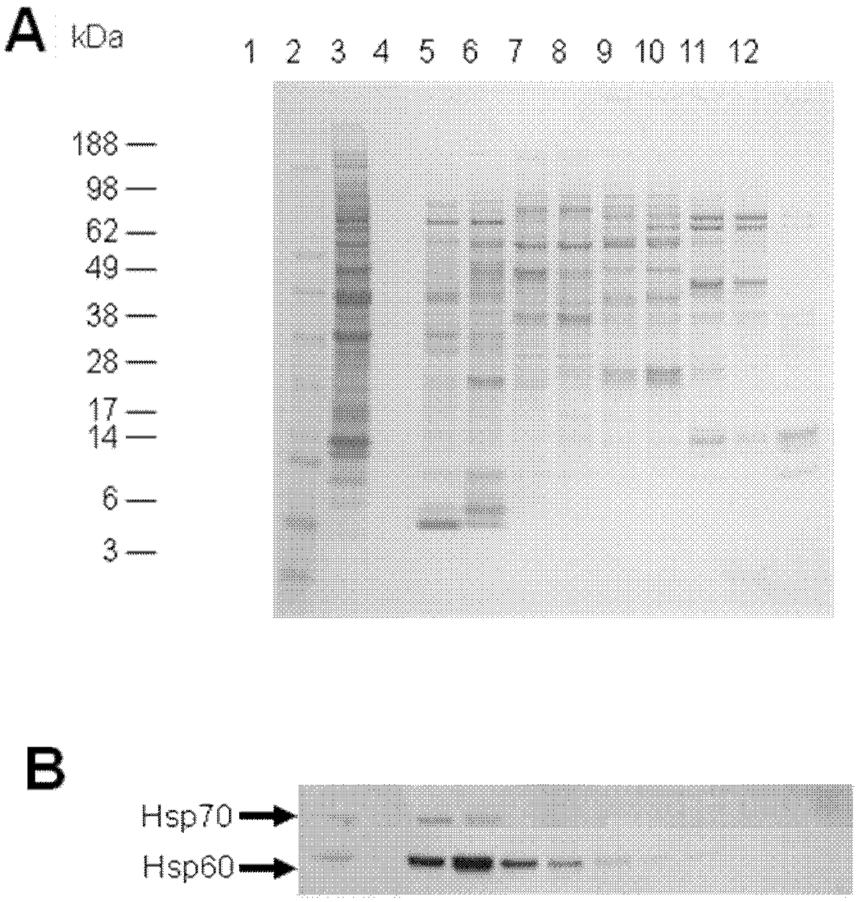
FIG. 8 shows the Coomasie Blue stained SDS-PAGE analysis of the purification of HEPs from CHO cells, eluted by a step salt gradient (A) and the analysis of these samples for the Hsp70 (B) and Hsp 60 (C) proteins by Western blotting. Lane 1—molecular weight (Mw) markers, lane 2 flow through, lane 3 wash, lane 4 150 mM elution, lane 5 150 mM elution, lane 6 250 mM elution, lane 7 250 mM elution, lane 8 350 mM elution, lane 9 350 mM, lane 10 500 mM elution, lane 11 500 mM elution, lane 12 1 M elution.

Immunogenicity of *Neisseria meningitides* HEPs and Induction of a Protective Immune Response Against Live Challenge The HEPs prepared from *Neisseria meningitidis* strain MC58 according to the method of Example 3 were used to immunise mice in order to generate sera for assessment of cross strain responses. Sera from immunised animals were pooled and assessed for their ability to elicit cross-strain antibody-mediated opsonophagocytosis using the following clinical *Neisseria meningitidis* (meningitis B, MnB) strains; MC58, H44/76-SL, M01-240101, M01-240013, M01-240149, M01-240185 and M01-240355. For assay, serum samples were incubated with killed BCECF-fluoresence labelled bacteria and IgG-depleted baby rabbit complement for 7.5 min at 37° C. HL60 cells differentiated with 0.8% DMF, were added and samples incubated for 7.5 min before the addition of ice cold DPBS to stop the reaction. Samples were analysed by flow cytometry and data expressed as a fluorescence index value (Fl-C'). For all strains, serum obtained from mice vaccinated with the MC58-derived HEPs induced oposonisation responses significantly greater than those obtained with serum from non-vaccinated controls and animals immunised with hspCs purified using conventional isoelectric focussing methods or with a commercial outer membrane vesicle (H44/76 OMV) vaccine candidate. The results obtained with the heterologous strain M01-240101 are shown in FIG. 5 and show the cross-strain protection obtained with the HEPs (IEC HspC), conventionally purified hspCs (IEF HspC) and the OMV vaccine (H44/76 OMV). The HEPs containing vaccine also generated higher opsonisation values than the IEF HspC vaccine against both MC58 and the H44/76 strain from which the OMV vaccine was derived. HEPs prepared from a large scale ferment culture of MC58 using IEC as in Example 3 with the use of 50 mM HEPES buffers at pH6.8 and a C5 Emulisflex homogeniser (Avestin Inc.) to lyse the cells were tested as vaccines against Meningitis in a lethal challenge mouse model using *N. meningitidis* strain 44/76-SL using high dose challenge with $0.8\times10^7$ live organisms. The protective immunogenicity of the HEPs isolated from *N. meningitidis* (MC58 HspC) against lethal challenge by a homologous strain was equivalent to that observed with the conventional outer membrane vesicle vaccine (OMV) in currently clinical use (FIG. 6) as assessed by both health scores (6A) or survival (6B). Importantly, the HEPs vaccines showed significantly better immunogenicity against heterologous strains than the OMV vaccines (FIG. 7).

Example 5

Protective Cross Serotype and Serogroup Immunogenicity of *N. meningitidis* HEPs Current meningitis B vaccines are made up from outer membrane vesicle preparations (OMV) isolated from *N. meningitidis* B serotype and show only poor cross serotype protection against other and no cross serogroup protection against meningitis A and C serogroups. HEPs vaccines isolated from *N. Meningitidis* B serotype H44/76-SL were compared to conventional OMV vaccines from H44/76-SL and protective immunogenicity assessed by oposonisation assay as validated in Example 4 above. The HEPs isolated from *N. Meningitidis* B serotype H44/76-SL elicited not only good cross serotype immunity (serotypes MC58 and 240-013,085, 101,149 and 355) but also showed good cross serogroup immunogenicity against Meningitis A (NmA) and Meningitis C (NmC) strains (FIG. 7). Moreover, the immunogenicity was significantly better than the currently clinically used OMV vaccines which show no cross serogroup immunogenicity and no cross serogroup immunogenicity (FIG. 7 HspC versus OMV).

Example 6

Purification and Immunogenicity of HEPs from Baculovirus Infected Insect Cells Recombinant baculovirus expressing influenza H3 Panama haemagglutinin and hepatitis C virus E1 and E2 polypeptides as fusion proteins with a human IgG Fc fragment were used to infected Sf9 insect cells. Infected cells were grown for 72 hours in Insect-Xpress protein-free media and cells pelleted at 4,500 rpm for 10 minutes in a Jouan GR422 centrifuge. Cell pellets were resuspended and lysed on ice in 10 mM Tris-HCl, pH 6.8 containing 0.2% NP40, 1 mg/ml pepstatin and 0.2 mM PMSF using a dounce homogenizer. The lysate was centrifuged at 12,000 g for 15 mins and the supernatant centrifuged at 100,000 g for 30 minutes to yield a clarified lysate which was then loaded onto a CaptoQ™ column. The column was washed in 10 mM Tris-HCl, pH 6.8 containing 100 mM NaCl and the HEPs eluted with a 150-350 mM NaCl salt gradient. The purified HEPs were used to immunise mice and rabbits and sera from the immunized animals assayed by Western blotting and inhibition of hemagglutination.

Example 7

Purification and Immunogenicity of HEPs from Tumour Cells

EL4 and A20 cells were grown in RPMI media, lysed in buffers containing non-ionic using a Potter homogeniser and tumour cell HEPs purified and tested for immunogenicity by Western blotting as in Example 5.

Example 8

Purification and Immunogenicity of HEPs from Host Cells Expressing Heterlogous Antigens CHO (Chinese hamster ovary) cells and CHO cells expressing Immunoglobulin Fc-fusion proteins were grown in CHO CD media (Gibco). CHO cells were harvested, washed in PBS, resuspended in 50 mM HEPES, 150 mM NaCl pH6.8 either with or without 1 mM ADP and 1 mM MgCl and lysed by sonication. The lysate was clarified by centrifugation followed by filtration through 0.8 μM and then 0.2 μM filters, diluted 10× in 50 mM HEPES pH6.8 and the HEPs purified using an AKTA chromatography system on a 1 ml CaptoQ column. The column was washed with 20 ml buffer containing 50 mM HEPES pH6.8 and B, 50 mM HEPES, 20 mM NaCl pH6.8 either with or without added 1 mM ADP and 1 mM MgCl and the HEPs eluted in wash buffer containing increasing salt concentration of 150 mM NaCl, 250 mM NaCl, 350 mM and 500 mM NaCl. HEPs were run on SDS-PAGE gels and either stained for protein with Coomassie (FIG. 6A) or Western blotted for either hsp60 (antibody SPA-875, Stressgene) or Hsp70 (antibody SPA-811, Stressgene) (FIGS. 6B and 6C respectively) showing good separation of the HEPs by step gradient elution from the CaptoQ column.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

The invention claimed is:

1. A method for purification of complexes formed between stress proteins of different stress protein families and an antigenic polypeptide or fragment thereof from a source mixture, wherein the polypeptide or fragment thereof is a tumor or pathogen polypeptide antigen, consisting of the steps of:

(i) providing the source mixture comprising target stress protein complexes which are to be purified from the source mixture wherein the target stress protein complexes are formed by proteins of different stress protein families complexed to the polypeptide or a fragment thereof, (ii) determining the isoelectric point (pI) of the target stress protein complexes;

(iii) preparing a cell lysate from the source mixture comprising the target stress protein complexes;

(iv) clarifying the cell lysate by subjecting the cell lysate to centrifugation and/or filtration to provide a clarified cell lysate;

(v) transferring the clarified cell lysate of step (iv) to an ion exchange column wherein the transferred clarified cell lysate comprises all the stress protein complexes found within the cell lysate of step (iii); and (vi) subjecting the clarified cell lysate of step (v) to purification using an ion exchange solid phase, wherein during ion exchange the clarified cell lysate is buffered using a buffer to a pH within 2 units of the pI of the target stress protein complexes, and wherein a salt gradient provided by an elution buffer having a pH of from pH 4 to pH 9 is used to elute the target stress protein complexes comprising the stress proteins of the different stress protein families complexed to the polypeptide or a fragment thereof from the ion exchange solid phase, wherein the eluted target stress protein complexes comprise stress proteins from different stress protein families.

2. The method as claimed in claim 1 wherein the cell lysate buffer does not include a chaotrope.

3. The method as claimed in claim 1 wherein the cell lysate buffer does not include an ampholyte.

4. The method as claimed in claim 1 wherein the cell lysate buffer does not contain a surfactant.

5. The method as claimed in claim 1 wherein the elution buffer comprises sodium chloride.

6. The method as claimed in claim 5 wherein the pH of the elution buffer is pH6.8.

7. The method as claimed in claim 1 wherein the ion exchange is selected from the group consisting of ion exchange chromatography, cation exchange chromatography, anion exchange chromatography and mixed mode chromatography.

8. The method as claimed in claim 1 wherein the stress protein complexes are eluted in an eluate fraction which comprise complexes with a pI of 4.5 to 6.5.

9. The method as claimed in claim 7 wherein the anion exchange chromatography is performed at a pH of from pH 5.0 to pH 9.0 and at a conductivity of from 0.5 to 5 mS/cm.

10. The method as claimed in claim 7 wherein the cation exchange chromatography is performed at a pH of from 4.0 to 9.0 and at a conductivity of from 0.5 to 15 mS/cm.

11. The method as claimed in claim 1 wherein the stress protein complexes are isolated from a cell selected from the group consisting of a cancerous cell, a pathogenic cell, a cell infected by a pathogenic organism, a cell which has been genetically modified such that it expresses a heterologous protein which is expressed by a cancerous cell, and a cell which has been genetically modified such that it expresses a heterologous protein expressed by a pathogen which causes an infectious disease in a host.

12. The method as claimed in claim 1 wherein the antigenic polypeptide or a fragment thereof of the stress protein complexes is from a pathogenic organism which causes an infectious disease in an infected host wherein the pathogenic organism is selected from the group consisting of a prokaryotic cell, a protozoa, a virus, a parasite and a fungi.

13. The method as claimed in claim 12 wherein the pathogenic organism is a gram positive bacteria or a gram negative bacteria.

* * * * *